United States Patent [19]

Arai et al.

[11] 3,935,015

[45] Jan. 27, 1976

[54] SILVER HALIDE COLOR PHOTOGRAPHIC MATERIALS CONTAINING 3-ANILINO-5-PYRAZOLANE COUPLERS

[75] Inventors: Atsuaki Arai; Yasushi Oishi; Akio Okumura; Minoru Yamada; Yukio Yokota; Kozo Inouye, all of Minami-Ashigara, Japan

[73] Assignee: Fuji Photo Film Co., Ltd., Minami-ashigara, Japan

[22] Filed: Feb. 22, 1974

[21] Appl. No.: 445,032

[30] Foreign Application Priority Data

Feb. 22, 1973 Japan.............................. 48-21454

[52] U.S. Cl. .......................... 96/74; 96/56; 96/100
[51] Int. Cl.² .................. G03C 1/76; G03C 1/40
[58] Field of Search ............... 96/100, 56.5, 56, 74

[56] References Cited
UNITED STATES PATENTS

| | | | |
|---|---|---|---|
| 2,311,082 | 2/1943 | Porter et al............................ | 96/100 |
| 3,127,269 | 3/1964 | Greenhalgh et al.................. | 96/100 |
| 3,419,391 | 12/1968 | Young.................................. | 96/100 |
| 3,519,429 | 7/1970 | Lestina................................. | 96/56 |
| 3,808,007 | 4/1974 | Meier et al. ......................... | 96/100 |

*Primary Examiner*—J. Travis Brown
*Attorney, Agent, or Firm*—Sughrue, Rothwell, Mion, Zinn & Macpeak

[57] ABSTRACT

A color photographic material having differently sensitized silver halide emulsion layers including a silver halide emulsion layer containing a 3-anilino-5-pyrazolone magenta dye-forming coupler, the coupler having a halogen atom or an alkoxyl group at the 2-position of the anilino group and an aliphatic acylamino group at the 5-position of the anilino group.

9 Claims, No Drawings

SILVER HALIDE COLOR PHOTOGRAPHIC MATERIALS CONTAINING 3-ANILINO-5-PYRAZOLANE COUPLERS

BACKGROUND OF THE INVENTION

1. Field of the Invention

This invention relates to a silver halide color photographic material containing an improved magenta dye-forming coupler.

2. Description of the Prior Art

It is well known that when silver halide photographic materials are color-developed after light-exposure, couplers contained in the color photographic materials react with the oxidation products of aromatic primary amino developing agents to provide indophenol, indoaniline, indamine, azomethine, phenoxazine, phenazine, and other similar dyes, whereby color images are formed. In such a known system, color reproduction is conducted by a subtractive color process and yellow, magenta, and cyan dye images corresponding to blue, green, and red light images, respectively, are formed. In general, an acylacetamide coupler or a dibenzoylmethane coupler is used for forming yellow dye images, a pyrazolone coupler, a cyanoacetyl coupler or an indazolone coupler is used for forming magenta dye images, and a phenolic coupler such as a phenol and a naphthol is used for forming cyan dye images.

Various 5-pyrazolone derivatives are known for forming magenta dye images for trichromatic color photography. For instance, as the substituents at the 3-position of the 5-pyrazolone ring, an alkyl group and an aryl group are known. Furthermore, as such substituents, alkoxyl groups as described in the specification of U.S. Pat. No. 2,439,098, acylamino groups as described in the specifications of U.S. Pat. Nos. 2,369,489 and 2,600,788 and ureido groups as described in the specification of U.S. Pat. No. 3,558,319 are known. Other examples of such substituent are anilino groups. For instance, 3-anilino-5-pyrazolone couplers are described in the specification of U.S. Pat. No. 2,311,081 (or Reissue No. 22,329) and also many improvements in such couplers have been proposed. As an example British Pat. No. 956,261 teaches that an azomethine dye obtained from a 3-anilino-5-pyrazolone derivative having an alkoxyl group or a halogen atom, as a substituent, at the ortho-position of the anilino group has particularly less unnecessary absorption in a red light region, which is a preferred spectral characteristic for color photography. As an example of non-diffusible couplers which belong to this type of coupler and which can be incorporated in photographic emulsions, the 3-(acylaminoanilino)-5-pyrazolones represented by the following general formula (M) are known:

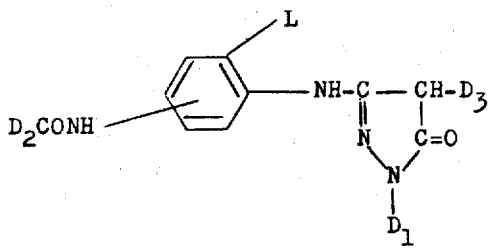

wherein $D_1$ represents an aryl group, $D_2CO-$ represents an acyl group, $D_3$ represents a hydrogen atom or a residue such as a phenoxy group which is released by the oxidation product of an aromatic primary amino developing agent, and L represents a chlorine atom or a methoxy group.

These couplers must be provided with diffusion resistance in order that these coupler are prevented from diffusing into other photographic emulsion layers having different spectral sensitivities and mixing with other couplers to reduce the color reproduction of the photographic emulsion layers by causing color mixing when these couplers are used in silver halide photographic emulsion layers of color photographic materials. For this purpose the introduction into the coupler molecule of a hydrophobic residue having more than 8 carbon atoms, which contributes to reducing the diffusibility of the coupler, as a ballasting group, is required.

To incorporate such non-diffusible couplers into photographic emulsions, the following three methods have generally been employed:

1. Aqueous solution system: The non-diffusible coupler having a water-solubilizing group such as a carboxyl group or a sulfo group and being soluble in an alkaline aqueous medium is incorporated in a photographic emulsion in the form of a neutral or alkaline aqueous solution thereof and then the emulsion is neutralized with an acid.

2. Oil solution system: The non-diffusible coupler is dissolved in an organic solvent, the solution is dispersed in an aqueous medium as fine colloidal particles, and the dispersion is added to a photographic emulsion.

3. The non-diffusible coupler is melted by heating and the molten coupler is directly dispersed in a photographic emulsion or aqueous medium.

Of these systems, the present invention is concerned with the aforesaid oil solution system (2). In order to form a green-sensitive photographic emulsion layer having excellent properties using a coupler forming magenta dye images employing the oil solution system, the coupler must satisfy the following conditions: that is to say, the coupler must have high coupling reactivity with the oxidation product of a developing agent, the magenta dye image formed by color development must have light absorption characteristics appropriate for the color reproduction principle of the trichromatic subtraction color process, the magenta dye image formed must have a high fastness so that the image can be stored under severe conditions without fading, the coupler must not adversely influence the properties of photographic emulsions, and further the coupler must be readily soluble in an organic solvent employed for dispersing the coupler in a photographic emulsion and be less crystallized in the solvent.

On the other hand, since conventionally known magenta dye-forming couplers in the oil solution system show insufficient reactivity with the oxidation product of developing agent in the dispersed state in photographic emulsion layers, it is difficult to obtain green sensitive emulsion layers having excellent photographic properties using the oil solution system.

Because a magenta dye image in a color photograph using the trichromatic subtraction color process absorbs light in the longest wave-length region of human visible sensitivity, the light absorption characteristics of the magenta dye image are a very important factor in determining the color reproduction properties of the color photograph. In particular, it has been believed that the improvement in the sharpness of spectral absorption curve and the reduction in the second absorption specific to pyrazolone magenta coupler give better absorption characteristics for the magenta dye image and various efforts have been made in this respect.

Also, when conventional magenta dye images formed from various magenta dye image-forming couplers are stored under high temperature and humidity conditions for a long period of time, they tend to fade and to prevent the occurence of such a tendency in the case of using conventional magenta dye-forming couplers, it is inevitable that formaldehyde be used in the course of development.

SUMMARY OF THE INVENTION

An object of this invention is to provide magenta dye imageforming couplers suitable for producing color photographic materials using the oil solution system.

Another object of this invention is to provide a color photographic material which can reproduce clear colors by the subtraction color process.

Still another object of this invention is to provide color photographs which have stable magenta dye images and which can be stored under severe conditions for a long period of time with less fading.

A further object of this invention is to provide color photographic materials suitable for simple development processing without the necessity for a stabilization treatment with formaldehyde, etc.

Another object of this invention is to provide color photographic materials containing magenta dye image-forming couplers which can be prepared easily using easily available raw materials.

The above and other objects of this invention will become apparent from the following detailed explanations and examples as set forth below.

The above-mentioned objects of this invention can be attained by incorporating, as a magenta dye-forming coupler, a 5-pyrazolone derivative in which the anilino group of a 3-anilino-5-pyrazolone is substituted with a halogen atom or an alkoxyl group at the 2-position thereof and with an aliphatic acylamino group at the 5-position. Also the 4-position of the pyrazolone can be substituted with a coupling releasable group.

That is to say, according to the present invention there is provided a color photographic material comprising a support having coated thereon a silver halide emulsion layer containing a 3-anilino-5-pyrazolone magenta dye-forming coupler, the coupler having a halogen atom or an alkoxyl group at the 2-position of the anilino group and an aliphatic acylamino group at the 5-position of the anilino group.

DETAILED DESCRIPTION OF THE INVENTION

The term "coupling releasable group" as used in this specification has the conventional meaning as used in the field of dye-forming couplers. Namely, the term means a group which is released by the oxidation product of an aromatic primary amino developing agent.

Pyrazolone couplers particularly useful in this invention include compounds represented by the following general formula (I):

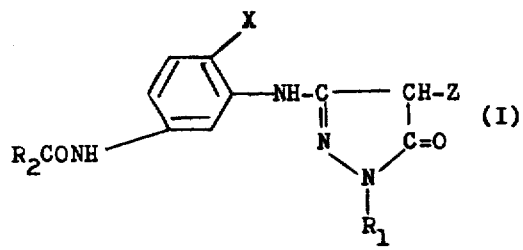

wherein $R_1$ represents an aryl group (such as, for instance, phenyl, halophenyl such as 2-chlorophenyl, 4-chlorophenyl, 2,5-dichlorophenyl, 2,6-dichlorophenyl, 2,4,6-trichlorophenyl, 2-bromophenyl, 3,5-dibromophenyl, etc., cyanophenyl such as 2-cyanophenyl, 4-cyanophenyl, etc., nitrophenyl such as 3-nitrophenyl, 4-nitrophenyl, etc., alkyl phenyl such as 4-methylphenyl, 2,6-dimethylphenyl, 2,6-dimethylphenyl, 4-butylphenyl, etc., fluoroalkylphenyl such as 2-trifluoromethylphenyl, etc., alkoxyphenyl such as 2-ethoxyphenyl etc. arylphenyl such as 4-phenylphenyl, etc., aryloxyphenyl such as 4-phenoxyphenyl, etc., N-substituted benzamidophenyl such as N-methylbenzamidophenyl, N,N-disubstituted carbamylphenyl such as N,N-diphenylcarbamylphenyl, etc., N,N-disubstituted sulfamylphenyl such as N,N-diphenylsulfamylphenyl, N,N-dibutylsulfamylphenyl, etc., phenyl-N-substituted sulfonamidophenyl such as phenyl-N-methylsulfonamidophenyl, etc., alkoxycarbonylphenyl such as methoxycarbonylphenyl, ethoxycarbonylphenyl, etc., aralkoxycarbonylphenyl such as benzyloxycarbonylphenyl, etc., carboxyphenyl such as 4-carboxyphenyl, etc., and various combinations of these, such as 2-methyl-5-nitrophenyl, 2-chloro-5-cyanophenyl, 5-chloro-2-methylphenyl, 2,6-dichloro-4-methylphenyl, 2,4-dichloro-6-methylphenyl, 2-chloro-4,6-dimethylphenyl, 2,6-dichloro-4-methoxyphenyl, 2,6-dichloro-4-nitrophenyl, 2,4,6-trimethyl-3-nitrophenyl, 2,6-dichloro-4-methoxycarbonylphenyl, 2,6-dichloro-4-benzyloxycarbonylphenyl, 2,6-dichloro-4-carboxyphenyl, 2,4,6-trimethyl-3-substituted aminophenyl, etc.,) or a heterocyclic ring group (such as, for example, 2-thiazolyl, 2-benzothiazolyl, 2-benzooxazolyl, 2-oxazolyl, 2-imidazolyl, 2-benzimidazolyl group, etc.,); $R_2$ represents a straight chain, branched chain, or cyclic alkyl group having 5 to 29 carbon atoms, preferably 7 to 23 carbon atoms, such as, heptyl, nonyl, undecyl, tridecyl, heptadecyl, 2-ethylhexyl, 2-hexyldodecyl, 4-hexylcyclohexyl, 3-pentadecylcyclohexyl, norbornyl, 7,7-dialkylnorbornyl, 2-pentadecyl, 7,7-dialkylnorbornyl, etc.; X represents an alkoxyl group having 1 to 18 carbon atoms or a halogen atom (such as, for example, fluorine, chlorine, bromine, etc.,); and Z represents a hydrogen atom or any of the groups found as substituents on the 4 position of any of the prior art dye-forming 5-pyrazolone couplers (colored or uncolored) and on competing 5-pyrazolone couplers including a thiocyano group, an acyloxy group (such as an alkoyloxy group having from 1 to 22 carbon atoms, e.g., acetoxy, 3-pentadecylphenoxyacetoxy, propionyloxy, hexanoyloxy, dodecanoyloxy, octadecanoyloxy, 3-phenylpropionyloxy, etc., an aryloyloxy group, e.g., a benzoyloxy group, 3-(2-carboxybenzamido)benzoyloxy, 3-(β-sulfopropionamido)-benzoyloxy, α-naphthoyloxy, β-naphthoyloxy, 2,4,6-trichlorobenzoyloxy, 4-ethoxybenzoyloxy, 4-fluorobenzoyloxy, 3-[γ-(2,4-di-t-amylphenoxy)butyramido]benzoyloxy, etc., a heterocycloyloxy group, e.g., a benzofuranyloyloxy group, a furanyloxy group, a thiazoloyloxy group, an oxazoloyloxy group, etc.), an aryloxy group, e.g., a phenoxy group, a naphthoxy group, etc., an alkoxy group, e.g., methoxy, butoxy, octadecyloxy, etc., chlorine, fluorine, a sulfo group, e.g., sulfo or alkali metal salt of the sulfo group, an arylazo group, e.g., a phenylazo (such as phenylazo, a tolylazo group, a chlorophenylazo group, a benzamidophenylazo group, an acetamidophenylazo group, a methoxyphenylazo group, a naphthylazo group, etc.), a 2-aminoarylazoxy group (e.g., 2-amino-4-methylphenylazoxy, 2-aminophenylazoxy, 2-amino-4-chlorophenylazoxy, etc.); a 2-amidoarylazoxy group (e.g., 2-acetamidophenylazoxy, 2-acetamido-4-methylphenylazoxy, 2-acetamido-4-chlorophenylazoxy, 2-palmitamidophenylazoxy, 4-methoxy-2-palmitamidophenylazoxy, 4-chloro-2-palmitamidophenylazoxy, etc.); a 2-aryltriazolyl group (e.g., 2-benzotriazolyl, 5-chloro-2-benzotriazolyl, 5-hydroxy-2-benzotriazolyl, 4,7-dinitro-2-benzotriazolyl, 5-methyl-2-benzotriazolyl, 6-methoxy-2-benzotriazolyl, 4-carboxyethyl-2-benzotriazolyl, 4-sulfoethyl-2-benzotriazolyl, 2-naphthotriazolyl, 4-methyl-2-naphthotriazolyl, 5-chloro-2-naphthotriazolyl, 5-hydroxy-2-naphthotriazolyl, 5-nitro-2-naphthotriazolyl, 5-sulfoethyl-2-naphthotriazolyl, 4-amino-2-naphthotriazolyl, benzo[1,2-d:4,5-d']-bistriazolyl, etc.), an alkyl group having from 1 to 22 carbon atoms, e.g., methyl, ethyl, propyl, octyl, decyl, octadecyl, and preferably an organic monothio group, such as an alkylthio group (usually having from 6 to 10 carbon atoms), an arylthio group (generally a phenyl or naphthyl), a cycloalkylthio group (generally having 5 to 6 carbon atoms in the ring), especially preferred is a carbon-containing hererocyclic monothio group (generally having a 5 to 6 membered ring containing at least one hetero nitrogen, oxygen or sulfur atom and preferably 1 to 4 hetero nitrogen atoms) including heterocyclic radicals such as tetrazolyls, triazinyls, triazolyls, oxazolyls, oxadiazolyls, diazolyls, thiazyls, thiadiazolyls, benzoxazolyls, benzothiazolyls, pyrimidyls, pyridinyls, quinolinyls, benzimidazolyls, etc., in which the aryl-, cycloalkyl- and heterocyclic- moieties of the monothio group are incapable of forming a chromophoric compound and are either unsubstituted or substituted with groups, such as nitro, halogen (chlorine, bromine, iodine, fluorine), lower alkyl, lower alkylamido, lower alkoxy, lower alkylsulfonamido, α-chloroacetylthio, lower alkylcarbamyl, amino, etc., typical monothio groups representing the above include alkylthio groups (e.g., hexylthio, octylthio, decylthio, etc.), an arylthio group (e.g., 2-nitrophenylthio), a cycloalkylthio group (e.g., cyclopentylthio, cyclohexylthio, etc.), a heterocyclicthio group (e.g., 2-benzothiazolylthio, 1-phenyl-5-tetrazolylthio, 1-(4-carbomethoxyphenyl)-5-tetrazolylthio, 5-phenyl-1,3,4-oxadiazolyl-2-thio, 2-phenyl-5-(1,3,4)-oxadiazolylthio, 2-benzoxazolylthio, 2-benzimidazolylthio, etc.)

Furthermore, other examples of the particularly useful pyrazolone couplers in this invention are the compounds represented by the following general formula (II)

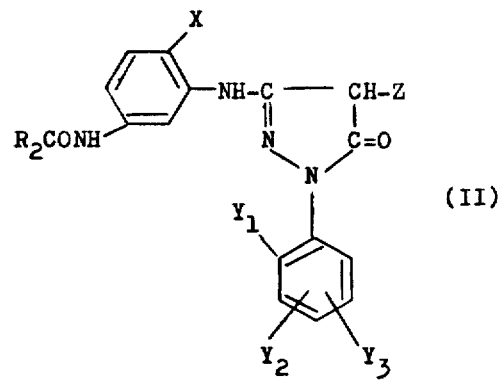

(II)

wherein $R_2$, X, and Z have the same significance as in general formula (I); $Y_1$ represents a halogen atom (such as, for example, fluorine, chlorine, bromine, etc.), and an alkyl group, or an alkoxyl group; and $Y_2$ and $Y_3$, which may be the same or different, each represents a hydrogen atom, a halogen atom, an alkyl group, an alkoxyl group, an aryloxyl group, an alkoxycarbonyl group, an aralkoxycarbonyl group, a carboxyl group, a cyano group, a nitro group, or an acylamino group.

The pyrazolone coupler in which at least one ortho position of phenyl group at the 1-position of the pyrazolone is substituted with a halogen atom, an alkyl group or an alkoxyl group as shown in general formula (II) has the advantage that even when the coupler remains in a color photographic material after development, less yellow color stains on the color image by the action of light or heat occur. Also, particularly preferable examples of the substituted phenyl group at the 1-position of the coupler represented by the general formula (II) are a 2,4-dichlorophenyl group, a 2,5-dichlorophenyl group, a 2,6-dichlorophenyl group, a 2,4,6-trichlorophenyl group, a 2,4-dibromophenyl group, a 2,5-dibromophenyl group, a 2,6-dichlorophenyl group, a 2,4,6-tribromophenyl group, a 2,4-dichloro-6-methylphenyl group, a 2,6-dichloro-4-methylphenyl group, a 2,4-dichloro-6-methoxyphenyl group, a 2,6-dichloro-4-methoxyphenyl group, a 2-chloro-4-nitrophenyl group, a 2-chloro-5-nitrophenyl group, a 2,6-dichloro-4-methoxycarbonylphenyl group, a 2,6-dichloro-6-dichloro-4-carboxyphenyl group, etc., since those pyrazolone couplers give less color stains on the coupler remaining and give dye images having preferable spectral absorption characteristics as magenta dye images with the subtractive color process (i.e., the absorption maximum is in the range of 530 millimicrons to 565 millimicrons and the absorption to blue and red light is less).

Also, as the alkyl groups represented by $R_2$, a straight chain alkyl group, preferably an alkyl group having an odd number of 7–17 carbon atoms is particularly desirable from the point that fatty acids available with low cost can be used as the starting materials for producing couplers having such alkyl groups. Still further, when a mixture of two or more such kinds of couplers having these straight chain alkyl groups is used, the solubility of the couplers in an organic solvent can be increased and the tendency of crystallization of the couplers in color photographic materials can be reduced.

Magenta dye-forming couplers which can be used in this invention are specifically illustrated below but the invention is not limited to only these couplers.

Coupler (1): 1-(2,4,6-Trichlorophenyl)-3-(2-chloro-5-n-tetradecanoylaminoanilino)-5-pyrazolone.

Coupler (2): 1-(2,4,6-Trichlorophenyl)-3-(2-methoxy-5-n-tetradecanoylaminoanilino)-5-pyrazolone.

Coupler (3): 1-(2,6-Dichloro-4-methoxyphenyl)-3-(2-chloro-5-n-tetradecanoylaminoanilino)-5-pyrazolone.

Coupler (4): 1-(2,4,6-trichlorophenyl)-3-(2-chloro-5-n-octadecanoylaminoanilino)-5-pyrazolone.

Coupler (5): 1-(2,4-Dimethyl-6-chlorophenyl)-3-(2-chloro-5-n-tetradecanoylaminoanilino)-5-pyrazolone.

Coupler (6): 1-(2,4-Dimethyl-6-chlorophenyl)-3-(2-methoxy-5-n-tetadecanoylaminoanilino)-5-pyrazolone.

Coupler (7): 1-(2,6-Dichloro-4-methylphenyl)-3-(2-methoxy-5-n-dodecanoylaminoanilino)-5-pyrazolone.

Coupler (8): 1-(2,6-Dichloro-4-methylphenyl)-3-(2-chloro-5-n-hexadecanoylaminoanilino)-5-pyrazolone.

Coupler (9): 1-(2,6-Dichloro-4-methoxyphenyl)-3-(2-methoxy-5-n-tetradecanoylaminoanilino)-5-pyrazolone.

Coupler (10): 1-(2,4,6-Trichlorophenyl)-3-(2-chloro-5-n-tetradecanoylaminoanilino)-4-α-naphthylazo-5-pyrazolone.

Coupler (11): 1-(2,4,6-Trichlorophenyl)-3-(2-chloro-5-n-tetradecanoylaminoanilino)-4-(4-methoxyphenylazo)-5-pyrazolone.

Coupler (12): 1-2,4,6-Trichlorophenyl)-3-(2-chloro-5-n-hexadecanoylaminoanilino)-4-(1-phenyl-5-tetrazolylthio)-5-pyrazolone.

Coupler (13): 1-(2,6-Dichloro-4-methoxyphenyl)-3-(2-chloro-5-n-tetradecanoylaminoanilino)-4-(4-methoxyphenylazo)-5-pyrazolone.

Coupler (14): 1-(2,4,6-Trichlorophenyl)-3-(2-methoxy-5-n-tetradecanoylaminoanilino)-4-α-naphthylazo-5-pyrazolone.

Coupler (15): 1-(2,4-Dimethyl-6-chlorophenyl)-3-(2-methoxy-5-n-dodecanoylaminoanilino)-4-(1-phenyl-5-tetrazolylthio)-5-pyrazolone.

Coupler (16): 1-(2,6-Dichloro-4-methoxycarbonylphenyl)-3-(2-chloro-5-n-tetradecanoylaminoanilino)-5-pyrazolone.

Coupler (17): 1-(2,6-Dichloro-4-benzyloxycarbonylphenyl)-3-(2-chloro-5-n-tetradecanoylaminoanilino)-5-pyrazolone.

Coupler (18): 1-(2-Chloro-3,5-dimethoxycarbonylphenyl)-3-(2-methoxy-5-n-hexadecanoylaminoanilino)-5-pyrazolone.

Coupler (19): 1-(2,6-Dichloro-4-n-butyloxycarbonylphenyl)-3-(2-chloro-5-n-octadecanoylaminoanilino)-5-pyrazolone.

Coupler (20): 1-(2,6-Dichloro-4-ethoxycarbonylphenyl)-3-(2-chloro-5-n-hexadecanoylaminoanilino)-4-(4-hydroxy-3-isobutylphenylazo)-5-pyrazolone.

Coupler (21): 1-(2,6-Dichloro-4-methoxycarbonylphenyl)-3-(2-chloro-5-n-tetradecanoylaminoanilino)-4-(1-piperidino)-5-pyrazolone.

The magenta dye-forming couplers used in this invention can be prepared using various methods. Specific examples of preparing typical couplers are shown below and other couplers can be prepared in a manner similar to the illustrated methods. Unless otherwise indicated in the examples given herein, all parts percents, ratios and the like are by weight.

SYNTHESIS EXAMPLE 1

Preparation of Coupler (1), 1-(2,4,6-Trichlorophenyl)-3-(2-chloro-5-n-tetradecanoylaminoanilino)-5-pyrazolone.

1. Preparation of 1-(2,4,6-trichlorophenyl)-3-(2-chloro-5-nitroanilino)-5-pyrazolone:

Method (a): A mixture was 94 g of $\beta,\beta$-diethoxyacrylic acid prepared using the method of S. A. Glickman et al; Journal of the American Chemical Society; Vol. 67, 1017 (1945) and 87 g of 2-chloro-5-nitroaniline was heated to 130°–150°C for 3 hours under stirring to form $\beta$-(2-chloro-5-nitroanilino)-$\beta$-ethoxyacrylic acid ester. The product thus obtained, without being isolated and purified, was mixed with 106 g of 2,4,6-trichlorophenylhydrazine and 750 ml of acetic acid and the mixture was refluxed for 2 hours. The reaction product was allowed to cool and then 750 ml of methanol was added to the reaction product to form precipitates, which were collected by filtration and washed with methanol to give 115 g of the desired product. The melting point of the product was 289°C.

Method (b): The above-described pyrazolone can be also prepared using the method described in the specification of U.S. Pat. No. 3,615,506. That is to say, a mixture of 154 g of 1-(2,4,6-trichlorophenyl)-3-ethoxy-5-pyrazolone and 130 g of 2-chloro-5-nitroaniline was heated to 140°C to form a uniform melt and then after adding 10 ml of methanesulfonic acid to the melt, the reaction was conducted at 140°–160°C for 1 hour under a reduced pressure while distilling off the ethanol formed with stirring. The reaction product was allowed to cool to 100°C and then after adding 250 ml of ethanol to the reaction product with stirring under heating, the mixture was allowed to cool to room temperature (about 20°–30°C) to form precipitates, which were collected by filtration and washed with 1 liter of methanol to give 151 g of the desired compound. The melting point of the product was 291°C.

2. Preparation of 1-(2,4,6-trichlorophenyl)-3-(2-chloro-5-aminoanilino)-5-pyrazolone:

434 g of 1-(2,4,6-trichlorophenyl)-3-(2-chloro-5-nitroanilino)-5-pyrazolone prepared by the aforesaid Method (a) or (b) was dispersed in a mixture of 2.5 liters of glacial acetic acid, 1.5 liters of methanol, and 300 ml of water and then 350 g of iron powder was added to the dispersion with stirring under heating over a period of 1 hour. The reaction product was poured in 15 liters of water and the precipitates thus formed were collected by filtration, washed with water, dried, and recrystallized from 8 liters of acetonitrile to give 293 g of the desired product having a melting point of 239°–241°C.

3. Preparation of 1-(2,4,6-trichlorophenyl)-3-(2-chloro-5-tetradecanoylaminoanilino)-5-pyrazolone:

101 g of 1-(2,4,6-trichlorophenyl)-3-(2-chloro-5-aminoanilino)-5-pyrazolone prepared in Method (2) as described above and 20 g of anhydrous sodium acetate were dispersed in a mixture of 1 liter of acetic acid and 500 ml of acetonitrile and then 65 g of myristic acid chloride was added dropwise to the dispersion with stirring at room temperature over a period of 30 minutes. The reaction product was poured into 20 liters of water and the precipitates thus formed were collected by filtration, dried, and recrystallized from a mixture of 200 ml of acetonitrile and 150 ml of ethanol to give 98 g of the desired product having a melting point of 115°–118°C.

SYNTHESIS EXAMPLE 2

Preparation of Coupler (1), 1-(2,4,6-Trichlorophenyl)-3-(2-chloro-5-tetradecanoylaminoanilino)-5-pyrazolone:

Using the same procedure as Method (a) of Synthesis Example 1, in place of 2-chloro-5-nitroaniline, 152 g of 2-chloro-5-tetradecanoylaniline was reacted with 94 g of $\beta,\beta$-diethoxyacrylic acid ethyl ester at 130°–150°C for 3 hours to give $\beta$-(2-chloro-5-tetradecanoylaminoanilino)-$\beta$-ethoxyacrylic acid ethyl ester. The product was, without being isolated and purified, mixed with 106 g of 2,4,6-trichlorophenylhydrazine and 500 ml of acetic acid and the mixture was refluxed for 2 hours. After distilling off the acetic acid from the reaction product mixture under a reduced pressure, a mixture of 300 ml of acetonitrile and 300 ml of ethanol was added to the reaction product followed by heating to dissolve the product therein and the solution was, then, allowed to cool to form precipitates, which were collected by filtration and recrystallized from a mixture of 150 ml of acetonitrile and 150 ml of ethanol to give 87 g of the desired product having a melting point of 115°–118°C.

SYNTHESIS EXAMPLE 3

Preparation of Coupler (2), 1-(2,4,6-Trichlorophenyl)-3-(2-methoxy-5-n-tetradecanoylaminoanilino)-5-pyrazolone:

1. Preparation of 1-(2,4,6-trichlorophenyl)-3-(2-methoxy-5-nitroanilino)-5-pyrazolone:

Using the same procedure as Method (a) in Synthesis Example 1, in place of 2-chloro-5-nitroaniline, 2-methoxy-5-nitroaniline was reacted with $\beta,\beta$-diethoxyacrylic acid ethyl ester and then the reaction product was further reacted with 2,4,6-trichloro phenylhydrazine to give the desired product having a melting point of 254°C.

2. Preparation of 1-(2,4,6-trichlorophenyl)-3-(2-methoxy-5-aminoanilino)-5-pyrazolone:

By reducing 1-(2,4,6-trichlorophenyl)-3-(2-methoxy-5-nitroanilino)-5-pyrazolone in the same way as Method (2) of Synthesis Example 1, the desired product was obtained. The melting point of the product was 203°–205°C.

3. preparation of 1-(2,4,6-trichlorophenyl)-3-(2-methoxy-5-tetradecanoylaminoanilino)-5-pyrazolone:

The 1-(2,4,6-trichlorophenyl)-3-(2-methoxy-5-aminoanilino)-5-pyrazolone prepared in the above procedure was reacted with myristic acid chloride prepared using Method (3) of Synthesis Example 1 to give the desired product having a melting point of 89°–93°C.

SYNTHESIS EXAMPLE 4

Preparation of Coupler (10), 1-(2,4,6-Trichlorophenyl)-3-(2-chloro-5-tetradecanoylaminoanilino)-4-$\alpha$-naphthylazo-5-pyrazolone:

An aqueous solution of $\alpha$-naphthyldiazonium hydrochloride prepared using a conventional method, as disclosed in U.S. Pat. 2,983,608 from 1.2 equivalents of $\alpha$-naphthylamine was added to a pyridine solution of 1-(2,4,6-trichlorophenyl)-3-(2-chloro-5-tetradecanoylaminoanilino)-5-pyrazolone at temperatures lower than 15°C and the yellow-orange precipitates thus formed were collected by filtration, washed with water and then methanol, and recrystallized from 1,2-dichloroethane to give the desired Coupler (10) having a melting point of 250°–253°C.

Since the magenta dye-forming couplers used in this invention have high coupling reactivity and sufficient solubility in organic solvents, the color photographic materials prepared using these couplers have good photographic properties such as sensitivity and gradation as well as can be prepared easily. In addition, the color photographic images obtained by developing the color photographic materials have preferred spectral absorption characteristics for color reproduction and sufficient fastness and further can be stored for a long period of time even under severe conditions. The features of this invention will further be explained below in detail.

Various 3-acylaminoanilino-5-pyrazolone couplers represented by aforesaid general formula (M) are described in British Pat. No. 956,261 but since the aliphatic hydrocarbon groups of those couplers are very short or the aliphatic hydrocarbon groups thereof have further been substituted and contain carboxyl groups, such couplers are not suitable for the objects of this invention and those known couplers are clearly distinguished from the pyrazolone couplers used in this invention. That is to say, the known couplers in which the aliphatic hydrocarbon groups are very short are dye-forming couplers of the type incorporated in color developers and are insufficient in diffusion resistance for the purposes of this invention. Also, the known couplers in which the aliphatic hydrocarbon groups have been substituted and contain carboxyl groups are water solution system couplers and thus have insufficient solubility in organic solvents.

The pyrazolone couplers used in this invention can be incorporated in the photographic emulsions using various techniques but typical examples are illustrated below.

a. A coupler is dissolved in an organic solvent, e.g., in an amount of 0.05 ml to 3 ml, preferably 0.2 to 1.5 ml, per gram of coupler which is sparingly soluble in water and has a high boiling point (higher than 200°C), the coupler solution is dispersed in an aqueous medium, and the dispersion is incorporated in a photographic emulsion.

Examples of organic solvents suitable for this method are phthalic acid dibutyl ester, phosphoric acid tricresyl ester, N,N-diethylcaproic acid amide, p-n-nonylphenol, 2-methyl-4-octylphenol, acetyltributyl citrate, tributylglycerol, etc.

b. A coupler is dissolved in an organic solvent which is comparatively less soluble in water, the coupler solution is dispersed in an aqueous medium, and the dispersion is incorporated in a photographic emulsion. The organic solvent used is removed during the production of photographic materials. Examples of solvents suitable for this method are ethyl acetate, cyclohexanone, β-n-butylethoxyethyl acetate, etc.

c. A coupler is dissolved in an organic solvent in an amount of about 0.5 ml to 10 ml, preferably 1 ml to 3 ml, per gram of coupler, which is miscible with water and the coupler solution is incorporated in a photographic emulsion. The organic solvent used can be removed during the production of photographic materials or can be allowed to remain in the photographic emulsion layers after the production of the photographic materials. Examples of solvents suitable for this method are dimethylformamide, dimethyl sulfoxide, N-methylpyrrolidone, glycerol, tetrahydrofuran, etc.

If desired, two or more kinds of the solvents used in aforesaid Methods (a), (b), and (c) can be used for improving the dispersing condition of the couplers.

In all cases, since the oil-soluble coupler is initially dissolved in an organic solvent or organic solvents and then incorporated in a photographic emulsion as a dispersion of the coupler solution in an aqueous medium, it is desired that the coupler have high solubility in organic solvents.

As oil-solubilizing groups for facilitating the dissolution of couplers used in the oil-solution system in organic solvents, various hydrophobic residues are known. Of them, the simplest hydrophobic residue is a straight chain alkyl group. However, a conventionally known coupler compound having a straight chain alkyl group having more than 8 carbon atoms bonded to the coupler residue has generally a melting point in a range of about 60° to about 120°C and heat of solution in a range of about 10 to about 18 Kcal/mol. This means that such a known coupler can be completely dissolved in an organic solvent at a temperature higher than 50°C but due to the large temperature dependence of the solubility, the solubility of the coupler is reduced greatly at low temperatures to which photographic materials are usually exposed and the coupler has a tendency of being crystallized, which results in reducing the properties of the photographic materials.

In order to overcome such difficulties hydrophobic groups having various types of substitution have been proposed. For instance, as the hydrophobic group capable of most highly reducing the heat of solution of couplers and providing couplers having excellent solubility at low temperatures, an alkylphenoxyalkyl group such as an α-(2,4,-di-tert-amylphenoxy)propyl group is known to be effective for phenol couplers, 1-naphthol couplers, acylacetamide couplers, and pyrazolone couplers. However, the aforesaid general rule about most couplers is inapplicable to the coupler nucleus of this invention shown by the formula

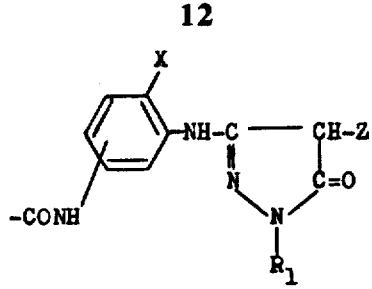

wherein $R_1$, Z, and X have the same significance as in general formula (I).

A coupler having the above-described coupler nucleus and an alkylaryloxyalkyl group is disclosed in U.S. Pat. No. 3,419,391 but such a coupler has a high melting point and poor solubility as will be explained hereinafter and is unsuitable for practical use.

On the other hand, a straight chain alkyl group which provides, in general, poor solubility to other kinds of couplers can provide a coupler, when it is applied to the coupler nucleus of this invention as described above, which has a melting point of about 100°C, which has a comparatively low heat of resolution of about 6–9 Kcal/mol at 25°C, and which can be dissolved quite well in a coupler solvent such as ethyl acetate. It is difficult to anticipate such a state of solubility from conventional knowledge of couplers having other types of nuclei and thus the combination of the coupler nucleus of this invention and the straight chain alkyl group is believed to be quite specific.

The excellent solubility of the couplers used in this invention is explained in detail below.

Coupler (1) of this invention: 1(2,4,6-Trichlorophenyl)-3-(2-chloro-5-n-tetradecanoylaminoanilino)-5-pyrazolone.

Coupler (4) of this invention: 1-(2,4,6-Trichlorophenyl)-3-(2-chloro-5-n-octadecanoylaminoanilino)-5-pyrazolone.

Comparison coupler (A): 1-(2,4,6-Trichlorophenyl)-3-(2-chloro-4-n-tetradecanoylaminoanilino)-5-pyrazolone.

Comparison coupler (B): 1-(2,4,6-Trichlorophenyl)-3-(2-methoxy-4-n-tetradecanoylaminoanilino)-5-pyrazolone.

Comparison coupler (C): 1-(2,4,6-Trichlorophenyl)-3-{5-[γ-(2,4-di-tert-amylphenoxy)butylamido]-2-chloroanilino}-5-pyrazolone.

Comparison coupler (D): 1-(2,4,6-Trichlorophenyl)-3-{5-[α-(2,4-di-tert-acylphenoxy)butylamido]-2-chloroanilino}-5-pyrazolone.

Comparison coupler (E): 1-(2,4,6-Trichlorophenyl)-3-{4-[α-(2,4-di-tert-acylphenoxy)butylamido]-2-methoxyanilino}-5-pyrazolone.

The solubility of these couplers in ethyl acetate (at 25°C) and the heat of solution of the couplers in ethyl acetate were measured, the results being shown in Table 1.

Table 1

| Coupler | (A)* | Structure of Hydrophobic Group | Melting Point (°C) | Solubility** | Heat of Solution (Kcal/mol) |
|---|---|---|---|---|---|
| Coupler (1) | 5 | Straight Chain alkyl: Group ($C_{14}$) | 115–118 | 32 | 5.13 |
| Coupler | 5 | ″ ($C_{18}$) | 91–94 | 14 | 8.46 |

Table 1-continued

| Coupler | (A)* | Structure of Hydrophobic Group | Melting Point (°C) | Solubility** | Heat of Solution (Kcal/mol) |
| --- | --- | --- | --- | --- | --- |
| (4) | | | | | |
| Coupler (A) | 4 | " ($C_{14}$) | 103–108 | 20 | 7.98 |
| Coupler (B) | 4 | " ($C_{14}$) | 113–114.5 | 68 | 5.02 |
| Coupler (C) | 5 | Alkylphenoxy-alkyl Group | 166–168 | 1 | *** |
| Coupler (D) | 5 | " | 203–205 | 4.5 | *** |
| Coupler (E) | 4 | " | 250–253 | 1.4 | *** |

(*): Position of the hydrophobic group on the anilide nucleus.
(**): Grams of coupler per 100 grams of solution.
(***): The solubility is too low to be measured.

The coupler used in this invention can be readily dissolved in a solvent due to its high solubility and hence the amount of the solvent necessary for dissolving the coupler can be reduced. Furthermore, in the case of using a conventional magenta coupler, in particular a pyrazolone magenta coupler in which the 3-position of the pyrazolone ring is substituted with an acylamino group or a ureido group, as the amount of a non-volatile high-boiling organic solvent incorporated in a photographic emulsion as the solvent for the coupler is reduced, the absorption of the dye image formed shifts completely to a markedly shorter wave length side and broadens as compared to a dye image in which a non-volatile high-boiling organic solvent remains sufficiently. Thus, there is a limit to ability to reduce the amount of the solvent for the coupler in the case of using such a conventional magenta coupler from the standpoint of the spectral absorption characteristics of dye images formed. On the other hand, in using the 3-anilino-5-pyrazolone coupler to which the couplers of this invention belong, the change of the spectral absorption characteristics of the dye images formed therefrom is much less when the content of the coupler solvent is reduced. In other words, the ability to reduce the amount of solvent is not restriced in this respect and, hence, it becomes easy to reduce the amount of the coupler solvent. Accordingly, when a non-volatile coupler solvent is used, the amount of the solvent retained in the coated photographic emulsion layers of photographic materials becomes less and the thickness of the photographic emulsion layers can be made thinner, which results in the formation of a sharp color image due to less scattering of light in the emulsion layers. Moreover, in the case of using the coupler of this invention, the coupler is less crystallized in a photographic emulsion containing it or in the dried photographic emulsion layers after coating.

The pyrazolone coupler used in this invention has at the 5-position of the anilino nucleus an acylamino group containing a hydrophobic group and has excellent coupler stability, the absorption characteristics of the dye formed as compared with a corresponding coupler in which the acylamino group is at the 4-position. If a (straight chain alkyl)—CONH— group is at the 4-position or the 5-position of the anilino nucleus, the pyrazolone coupler has good solubility in both cases but the coupler having the group at the 5-position is superior in color hue and stability. The features of a coupler in which the acylamino group is at the 5-position are further explained below more in detail.

In German Offenlegungsschrift 2,133,655, 1-(2,4-dimethyl-6-chlorophenyl)-3-{2-chloro-4-[α-(2-n-dodecyloxyphenoxy)butylamido]-anilino}-5-pyrazolone (Comparison coupler (F)) is described as a coupler having an oil-solubilizing group represented by the general formula

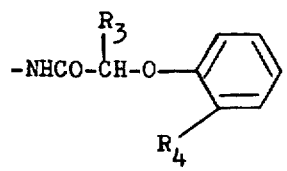

wherein $R_3$ represents a hydrogen atom or a lower alkyl group and $R_4$ represents an aliphatic hydrocarbon group having 8 to 16 carbon atoms and further in Japanese patent publication No. 19,032/1971, 1-(2,4,6-trichlorophenyl)-3-{2-chloro-4-[γ-(dodecyloxycarbonyl)-polyamido]anilino}-5-pyrazolone (Comparison coupler (G)) is described as a coupler having an oil-solubilizing group represented by the general formula

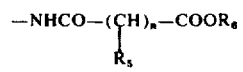

wherein $R_5$ represents an aliphatic hydrocarbon group having 1 to 4 carbon atoms and $R_6$ represents an aliphatic hydrocarbon group having 7 to 18 carbon atoms.

Both of these couplers are clearly different from the magenta coupler used in this invention in structure and further in those known couplers, the oil-solubilizing group is at the 4-position of the anilino group.

In regard to the above described two kinds of couplers and Comparison coupler (A), Comparison coupler (H), and couplers (1) and (5) of this invention, the spectral absorption characteristics of the azomethine dyes formed by the oxidative coupling reaction thereof with 4-{N-ethyl-N-(β-methanesulfonamidoethyl-)}amino-2-methylaniline in ethyl acetate were measured. From the spectral absorption curve thus obtained, the main wave length density was controlled to 100 and then the second absorption density in a blue light region, the density at the wave length side of 60 millimicrons longer than the main wave length, and the wave length width when the density became 0.50 were measured. The results obtained are shown in Table 2.

group at the 3-position of the anilino nucleus are faded to a great extent by heat. This is believed to result from the reaction of the dye formed with the coupler remain- Table 2

|  | Coupler | (1)* | (II)** | (a) | (b) | (c) |
|---|---|---|---|---|---|---|
| 3-Anilino pyrazolone | Coupler (1) | 2,4,6-Trichlorophenyl | 5 | 0.141 | 0.134 | 66 |
|  | Coupler (A) | " | 4 | 0.159 | 0.167 | 70 |
|  | Coupler (G) | " | 4 | 0.147 | 0.165 | 70 |
|  | Coupler (5) | 2,4-Dimethyl-6-chlorophenyl | 5 | 0.176 | 0.125 | 66 |
|  | Coupler (F) | " | 4 | 0.239 | 0.260 | 75 |
| 3-Acylaminopyrazolone | Coupler (H) | 2,4,6-Trichlorophenyl |  | 0.230 | 0.235 | 82 |

(1)*: Substituent at the 1-position of the pyrazolone ring.
(II)**: The position of the hydrophobic group on the anilido nucleus.
(a): Second absorption density
(b): Density at the wave length side of 60 millimicrons longer.
(c): Wave length at density 0.5.

From the results shown in the above table, it can be understood that the couplers of this invention have superior spectral absorption characteristics to not only known coupler (H) but also comparison couplers (A), (G), and (F).

The color images obtained from the magenta couplers used in this invention have spectral absorption curves sharply cut at the longer wave side and have less unnecessary second absorption, which are preferable in color reproduction. This is believed, as is clear from a comparison of Coupler (1) and Comparison coupler (A) each having the same oil-solubilizing group, to be a result of the oil-solubilizing group being at the 5-position of the anilino group in the coupler of this invention which differs from Comparison couplers (G) and (F).

Furthermore, the pyrazolone coupler having an —NHCOR type oil-solubilizing group at the 4-position of the anilino nucleus can be considered to be a p-phenylenediamine derivative and it is believed that such a compound is inferior in stability to oxidation to a coupler having a —NHCOR type oil-solubilizing group at the 5-position of the anilino nucleus. In fact, when 0.5 g of each of Coupler (1), Comparison coupler (A), Coupler (5), Comparison coupler (F), and Comparison coupler (G) was dissolved in 10 ml of tricresyl phosphate, and the solution was allowed to stand for 1 week at 40°C, the solution of Comparison coupler (A), (F), or (G) became dark brown at the interface of the surface of the solution and air, while no such phenomenon was observed in the solution of Coupler (1) or (5) of this invention. This shows that stains during manufacturing of photographic emulsions and after coating the photographic emulsions due to air exposure can possibly result in using a magenta coupler having an oil-solubilizing group at the 4-position of the anilino nucleus, as in Comparison couplers (A), (G), and (F).

The magenta dye images obtained from the magenta couplers used in this invention are not only fast to heat and moisture but also are less faded when exposed to intense light. On the other hand, it is known that the color images obtained from a conventional 5-pyrazolone coupler having an acylamino group or a ureido group at the 3-position of the anilino nucleus are faded to a great extent by heat. This is believed to result from the reaction of the dye formed with the coupler remaining to form a colorless product. In order to prevent fading, a treatment using a stabilizer containing formaldehyde, etc., has generally been conducted but in the case of using the pyrazolone coupler of this invention, a magenta dye image having sufficient fastness to heat and moisture is obtained without the necessity of such a treatment, which is one of the features of this invention. The stability to heat will be described in Example 2 shown later. As described above, the color photographic materials of this invention do not require any post treatment with formaldehyde, etc., and thus in using the color photographic materials of this invention, the development procedures can be simplified overall.

For producing the silver halide color photographic materials using the magenta dye-forming couplers of this invention, the pyrazolone couplers represented by general formula (I) can be used individually or as a mixture of two or more couplers or further they may be used together with magenta-dye forming coupler or couplers other than the couplers represented by general formula (I). Also, the pyrazolone coupler of this invention can be used in a same photographic emulsion for a magenta dye-forming coupler of the aqueous solution system. Furthermore, as described in the specification of Japanese patent publication No. 391/1965, the magenta coupler of general formula (I) can be used in a photographic emulsion containing a cyan coupler or a yellow coupler to improve the color reproducing characteristics of color photographic materials.

The photographic emulsion containing the magenta coupler of this invention in an amount of 1/20 mol to 1/500 mol, preferably 1/20 mol to 1/300 mol, of coupler per mole of silver present in the emulsion can be applied to a conventional photographic support in an amount of $1 \times 10^{-4}$ mol to $3 \times 10^{-3}$ mol/m$^2$, preferably $3 \times 10^{-4}$ mol to $2 \times 10^{-3}$ mol of coupler per m$^2$ of the support to provide various color photographic materials such as color positive films, color negative films, color reversal films, color photographic papers, and the like. Suitable supports which can be used for the light-sensitive material of the invention can be any kind of supports known in the photographic art, for example, plastic films such as cellulose acetate, polycarbonate, polyethylene terephthalate or polystyrene, baryta papers, polyethylene-laminated papers described in U.S. Pat. No. 3,253,922 or glass plates. These color photographic materials are, for example, described in U.S. Pat. Nos. 3,582,322; 3,622,318; 3,547,640; 3,672,898; 3,516,831; 3,705,799 − 803; 3,703,375; 3,379,529; 3,639,417; 3,402,046; and 3,450,536; U.S. patent application Ser. No. 206,060, filed Dec. 8, 1971; and Ser. No. 29,666, filed Apr. 17, 1970 and British Pat. No. 923,045.

As the silver halide for the aforesaid photographic emulsion in which the magenta coupler of this invention is incorporated, silver chloride, silver bromide, silver iodide, silver chlorobromide, silver chloroiodide, and silver chlorobromoiodide can be used. Also, the so-called converted halide silver halide grains as described in U.S. Pat. No. 3,622,318 and British Pat. No. 635,841 can be used. The photographic emulsion can further contain the natural sensitizers present in gelatin, sulfur sensitizers, noble metal salt sensitizers, and reduction sensitizers. Suitable examples of chemical sensitizers are described in U.S. Pat. Nos. 1,547,944, 2,410,689, 2,399,083, 2,642,361, 2,487,850, and 2,521,925, etc. Furthermore, in order to provide appropriate color sensitivity to the photographic emulsion, an optical sensitizer can be further added to the photographic emulsion. Suitable examples of optical sensitizers are disclosed in U.S. Pat. Nos. 2,519,001, 2,739,964, 3,481,742, 2,734,900, etc. Moreover, the photographic emulsion containing the coupler of this invention can contain an antifoggant as described in U.S. Pat. Nos. 3,420,668, 3,622,339, 2,697,099, 2,824,001, 2,694,716, etc., a stabilizer, an irradiation preventing dye, a coating aid as described in U.S. Pat. Nos. 2,288,226, 3,210,191, 3,294,540, 3,475,174, 3,545,974, etc., a polymer, a gelatin plasticizer such as dibutylphthalate, tricresylphosphate, dibutylsebacate, butylstearate, etc., a hardening agent. As disclosed in U.S. Pat. Nos. 3,232,764, 3,635,718, 3,100,704, 3,543,295, 3,288,775, and British Pat. No. 1,167,207.

It is preferable, for further increasing the stability of the color photograph obtained from the color photographic material of this invention, that the silver halide emulsion layer of the color photographic material containing the 3-anilino-5-pyrazolone coupler represented by general formula (I) contains additionally a p-substituted phenol derivative. Specific examples of p-substituted phenol derivatives suitable for the color photographic materials of this invention are hydroquinone derivatives including alkylhydroquinones, arylhydroquinones, dialkylhydroquinones, diarylhydroquinones, bihydroquinones, 6-hydroxychromans, 5-hydroxycoumarans, 6,6'-dihydroxy-2,2'-spirochromans, p-alkoxyphenols, p-aryloxyphenols, and alkoxyhydroquinones, as disclosed in U.S. Pat. Nos. 2,360,290; 2,418,613; 2,675,314; 2,701,197; 2,704,713; 2,728,659; 2,732,300; 2,735,765; 2,710,801; 2,816,028, and 3,700,453, the gallic acid derivatives as disclosed in U.S. Pat. Nos. 3,457,079 and 3,069,262 and the p-alkoxyphenols as disclosed in U.S. Pat. Nos. 2,735,765 and 3,698,909 and the p-oxyphenol derivatives as disclosed in U.S. Pat. Nos. 3,432,300; 3,573,050; 3,574,627, and 3,764,337.

The hydrophilic colloid layer, in particular, a gelatin layer containing the 3-anilino-5-pyrazolone coupler of this invention can be hardened using various kinds of cross-linking agents. For instance, an inorganic compound such as a chromium salt and a zirconium salt, mucochloric acid, or a aldehyde-type cross-linking agent such as 2-phenoxy-3-chloro-malealdehydic acid as described in Japanese patent publication No. 1872/1971 can be effectively used in this invention but the non-aldehyde type cross-linking agents such as the polyepoxy compounds as described in Japanese patent publication No. 7133/1959, the poly(1-aziridinyl) compounds as described in Japanese patent publication No. 8790/1962, and the active halogen compounds as described in U.S. Pat. Nos. 3,362,827 and 3,325,287 are particularly useful in the practice of this invention.

The color photographic materials containing the above-described pyrazolone couplers of this invention can be processed using conventional processing. That is to say, after exposure, the color photographic material of this invention can be developed in a developer containing a p-phenylenediamine developing agent and then bleached and fixed or blixed to provide a color image having excellent spectral absorption characteristics and transparency. Specific examples of developing agents suitable for developing the color photographic materials of this invention are 4-(N,N-diethylaminoaniline, 4-(N-ethyl-N-β-methanesulfonamidoethyl)amino-2-methylaniline, 4-(N-ethyl-N-β-hydroxyethyl)amino-2-methylaniline, 4-(N,N-diethylamino)-2-methylaniline.

Specific examples of this invention are described below but the invention is not intended to be interpreted as being limited to them. Unless otherwise indicated all parts, percents, ratios and the like are by weight.

EXAMPLE 1

A solution prepared by heating a mixture of 5 g of Coupler (3) of this invention, 2.5 ml. of tricresyl phosphate, and 10 ml of ethyl acetate to 60°C was added to 50 ml of an aqueous solution containing 5 g of gelatin and 0.15 g of sodium dodecylbenzenesulfonate at 60°C and then the mixture was stirred using a homogenizer to provide a dispersion of the coupler. The coupler dispersion thus prepared was added to 100 g of a photographic emulsion containing $5.6 \times 10^{-2}$ mol of silver chlorobromide (silver chloride 55 mol%) and 10 g of gelatin and then after adding thereto 5 ml of a 3% acetone solution of triethylene sulfamide as a hardening agent and finally adjusting the pH of the mixture to 6.5, the mixture was coated on a cellulose triacetate film and dried (dry thickness of the coated layer was 4.5 microns).

The color photographic film thus prepared was exposed conventionally and subjected to the following processing to provide a clear magenta dye image having an absorption maximum at 540 millimicrons.

| | Processing Step | Temperature | Time |
|---|---|---|---|
| 1. | Color Development | 21°C | 14 minutes |
| 2. | Washing | " | 30 seconds |
| 3. | First Fixing | " | 4 minutes |
| 4. | Washing | " | 4 minutes |
| 5. | Bleach | " | 8 minutes |
| 6. | Washing | " | 4 minutes |
| 7. | Second Fixing | " | 4 minutes |
| 8. | Washing | " | 6 minutes |

The compositions of the processing solutions used in the above processings were as follows:

| Color Developer: | | |
|---|---|---|
| 4-(N,N-Diethylamino)-2-methylaniline hydrochloride | | 2.5 g |
| Sodium Sulfite (Anhydrous) | | 10 g |
| Sodium Carbonate (monohydrate) | | 47 g |
| Potassium Bromide | | 2 g |
| Water added to make | (pH 10.5) | 1 liter |
| Fix Solution: | | |
| Sodium Thiosulfate | (6 H$_2$O) | 80 g |
| Sodium Sulfite (anhydrous) | | 5 g |
| Borax | | 6 g |
| Glacial Acetic Acid | | 4 ml |
| Potassium Alum | | 7 g |
| Water added to make | (pH 4.5) | 1 liter |
| Bleach Solution: | | |
| Potassium Ferricyanide | | 100 g |
| Potassium Bromide | | 5 g |
| Boric Acid | | 10 g |
| Borax | | 5 g |
| Water added to make | (pH 7.2) | 1 liter |

EXAMPLE 2

A polyethylene coated paper was coated with a blue-sensitive silver chlorobromide emulsion (silver bromide 70 mol%) containing α-pivaloyl-α-(5,5-dimethyl-3-hydantoinyl)-2-chloro-5-[α-(2,4-ditert-acylphenoxy)butylamido]-acetanilide as a yellow dye forming coupler as a first layer in a thickness of 3.0 microns to provide 3.53 × 10$^{-3}$ mol/m$^2$ of silver halide and 1.18 × 10$^{-3}$ mol/m$^2$ of the yellow dye forming coupler and then gelatin as a second layer in a thickness of 1.5 microns.

A solution obtained by heating to 60°C a mixture of 4.5 g of Coupler (4) of this invention, 0.3 g of 2,5-di-tert-octylhydroquinone, 0.4 g of 6,6'-dihydroxy-7,7'-dimethoxy-4,4,4,4'-tetramethylbis-2,2'-spirocoumarone, 4.0 ml of tricresyl phosphate, and 12 ml of ethyl acetate was added to 40 ml of an aqueous solution containing 4 g of gelatin and 0.10 g of sodium dodecylbenzenesulfonate at 60°C and the mixture was stirred using a homogenizer to provide a coupler dispersion. The coupler dispersion was added to 100 g of a green-sensitive photographic emulsion containing 4.70 × 10$^{-2}$ mol of silver chlorobromide (silver chloride 50 mol%) and 9 g of gelatin and then after adding thereto 5 ml of a 3% acetone solution of triethylene phosphamide as a hardening agent and finally adjusting the pH thereof to 7.0, the resultant mixture was coated on the second layer as a third layer in a thickness of 3.4 microns to provide 4.12 × 10$^{-3}$ mol/m$^2$ of silver halide and 5.89 × 10$^{-3}$ mol/m$^2$ of Coupler (4). Then, a gelatin solution containing 120 g of gelatin, 30 g of 2-(5-chlorobenzotriazole-2-yl)-4-methyl-6-tert-butylphenol and 50 g of 2-(benzotriazole-2-yl)-4-tert-butylphenol was coated as a fourth layer in a thickness of 1.5 microns, and further a red-sensitive emulsion containing silver chlorobromide (silver bromide 50 mol%) and 2-[α-(2,4-di-tert-amylphenoxy)-butylamido]-4,6-dichloro-5-methylphenol as a cyan coupler was coated as a fifth layer in a thickness of 2.5 microns, providing 2.94 × 10$^{-3}$ mol/m$^2$ of silver halide and 0.98 × 10$^{-3}$ mol/m$^2$ of the cyan coupler and finally a gelatin solution was coated as the uppermost layer in a thickness of 1 micron to provide a color print paper (Sample L).

Furthermore, using the same procedures as above except that 4.3 g of a known coupler (Coupler (H)), 1-2,4,6-trichlorophenyl)-3-{3-[α-(2,4-di-tert-amylphenoxy)butylamido]benzamido}-5-pyrazolone was used in place of Coupler (4) as the magenta dye-forming coupler and 6.0 ml of dioctylbutyl phosphate was used in place of tricresyl phosphate, a comparison color print paper was prepared (Sample M).

Each of the samples thus prepared was step exposed to green light and then subjected to the following processing.

| Processing Step | Temperature | Time |
|---|---|---|
| 1. Color Development | 30°C | 4 minutes |
| 2. Blix | " | 2 minutes |
| 3. Washing | " | 2 minutes |
| 4. Stabilization | " | 2 minutes |

The compositions of the processing solutions used in the above processing were as follows:

| Color Developer: | |
|---|---|
| Sodium Metaborate | 25 g |
| Sodium Sulfite | 2 g |
| Hydroxylamine (sulfate) | 2 g |
| Potassium Bromide | 0.5 g |
| 6-Nitrobenzimidazole (nitrate) | 0.02 g |
| Sodium Hydroxide | 4 g |
| Benzyl Alcohol | 15.8 ml |
| Diethylene Glycol | 20 ml |
| 4-(N-Ethyl-N-β-methanesulfoneamidoethyl)-amino-2-methylaniline Sesquisulfate | 8 g |
| Water added to make | 1 liter |
| Blix Solution: | |
| Sodium Ferric Ethylenediamine Tetraacetate | 45 g |
| Ammonium Thiocyanate | 10 g |
| Sodium Sulfite | 10 g |
| Ethylenediamine Tetraacetic Acid, Tetrasodium Salt | 5 g |
| Ammonium Thiosulfate (60%) | 100 ml |
| Water added to make | 1 liter |
| Stabilization Bath (a): | |
| Tartaric Acid | 10 g |
| Zinc Sulfate | 10 g |
| Sodium Metaborate | 20 g |
| Water added to make | 1 liter |
| Stabilization Bath (b): | |
| Tartaric Acid | 10 g |
| Zinc Sulfate | 10 g |
| Sodium Metaborate | 20 g |
| Formalin (40%) | 10 ml |
| Water added to make | 1 liter |

Sample L gave, using the above-described development processing including the stabilization bath (a), a magenta dye-forming image having an absorption maximum at 540 millimicrons and Sample M gave also a magenta dye-forming image having an absorption maximum at 540 millimicrons. Then these color images thus formed were stored for 4 hours at 120°C, for 2 weeks at 60°C and 75% RH, or for 2 weeks under exposure to a fluorescent lamp through a filter which absorbed substantially all ultraviolet light having wave lengths of shorter than 400 millimicrons and the density reduction (%) of the magenta dye images from the initial density were measured. The results obtained are shown in Table 3.

Table 3

| | Density Reduction (%) | | | | | |
|---|---|---|---|---|---|---|
| | (a) | | (b) | | (c) | |
| Initial Density | 0.5 | 1.0 | 0.5 | 1.0 | 0.5 | 1.0 |
| Sample L, Stabilization Bath (a) | 9 | 5 | 22 | 17 | 8 | 7 |

Table 3-continued

| | Density Reduction (%) | | | | | |
|---|---|---|---|---|---|---|
| | (a) | | (b) | | (c) | |
| Sample M, Stabilization Bath (a) | 60 | 37 | 31 | 24 | 30 | 16 |
| Sample M, Stabilization Bath (b) | 8 | 4 | 28 | 22 | 9 | 5 |

(a): for 4 hours at 120°C,
(b): for 2 weeks under exposure to fluorescent lamp through the filter,
(c): for 2 weeks at 60°C and 75% RH.

The above results show that the coupler used in this invention gave a color image having high fastness to heat and moisture without the necessity of the use of a stabilization bath containing formaldehyde.

Also, color prints were made by exposing each of the color photographic papers prepared in the above procedure through a transparency having a color negative image and developing the color paper. The red portion of the color print obtained from Sample L of this invention had less darkness and was clearer than the color print obtained from Sample M containing the known compound.

EXAMPLE 3

A solution prepared by heating to 60°C a mixture of 4 g of Coupler (1), 8 ml, 5.6 ml, 3.2 ml, 2 ml, 0.8 ml, or 0 ml of tricresyl phosphate, and 6 ml, 8.5 ml, 11 ml, 12.5 ml, 15 ml, or 15 ml, respectively, of ethyl acetate was added to 40 ml of an aqueous solution containing 4 g of gelatin and 0.10 g of sodium dodecylbenzenesulfonate at 60°C and the mixture was stirred using a homogenizer to provide a coupler dispersion. Then, the resultant coupler disperrison was mixed with 100 g of a photographic emulsion containing $5.0 \times 10^{-2}$ mol of silver chlorobromide (silver chloride 55 mol%) and 9 g of gelatin and after adding thereto the hardening agent as set forth in Example 1 and adjusting the pH of the mixture to 6.5, the mixture was coated on a cellulose triacetate film base in an amount of $9.7 \times 10^{-3}$ mol/m² of silver halide and dried.

By following the same procedure as described above, a coupler dispersion was prepared using a mixture of 4 g of Coupler (H) used in Example 2 as a known coupler, 8 ml, 5,6 ml, 3.2 ml, 2 ml, 0.8 ml, or 0 ml of tricresyl phosphate and 6 ml, 8.5 ml, 11 ml, 12.5 ml, 14 ml, or 15 ml, respectively, of ethyl acetate and the coupler dispersion was mixed with 88 g of the photographic emulsion having the same composition as described above. The mixture was coated on a cellulose triacetate film as in the above manner and dried.

Each of the color photographic films thus prepared was developed in a developer having the following composition for 12 minutes at 21°C and then fixed, bleached, and fixed as described in Example 1 to provide a magenta dye image. The main absorption wave length peak of each magenta dye image and the fading percentage of the color image when the sample was stored for 4 hours at 120°C as described in Example 2 were measured. The results obtained are shown in Table 4.

| Color Developer: | | |
|---|---|---|
| Sodium Hexametaphosphate | 2 | g |
| Sodium Sulfite (anhydrous) | 2 | g |
| Benzyl Alcohol | 5 | ml |
| Sodium Carbonate (monohydrate) | 27.5 | g |
| Potassium Bromide | 0.5 | g |
| Hydroxylamine Sulfate | 2.5 | g |
| 4-{N-Ethyl-N-(β-methanesulfonamido-ethyl)}amino-2-methylaniline Sesquisulfate | 2.5 | g |

Also, a coupler dispersion was prepared in the same manner as described above using a mixture of 4 g of Coupler (1) of this invention, Comparison Coupler (C), or Comparison Coupler (H), tricresyl phosphate, and ethyl acetate in the various amounts as above and after storing the coupler dispersion for 3 weeks in a cold chamber of 5°C, 150 ml of water was added to the dispersion. The mixture was stirred for 24 hours at 40°C, filtered using filter paper, Toyo Roshi No. 5B, the filter paper was dried, and then the weight of the solid material remaining on the filter paper was measured. The results obtained are also shown in Table 4.

Table 4

| Ratio (ml/g) | Main Wave Length Peak (mμ) | | Heat Fastness (reduction in density by %) | | | | Stability of Emulsion (mg) | |
|---|---|---|---|---|---|---|---|---|
| | Coupler (1) | Coupler (H) | Coupler (1) | | Coupler (H) | | Coupler (1) | Coupler (C) |
| | | | Initial Density | | Initial Density | | | |
| | | | $D_{0.5}$ | $D_{1.0}$ | $D_{0.5}$ | $D_{1.0}$ | | |
| 2 | 540 | 546 | 4 | 4 | 45 | 41 | 5.5 | 37 |
| 1.4 | 540 | 547 | 6 | 5 | 53 | 45 | 6.1 | 55 |
| 0.8 | 540 | 548 | 8 | 7 | 62 | 49 | 5.0 | 124 |
| 0.5 | 540 | 550 | 10 | 6 | 67 | 53 | 6.0 | 219 |
| 0.2 | 542 | 553 | 11 | 10 | 77 | 58 | 8.0 | 423 |
| 0 | 544 | | 18 | 18 | 79 | 61 | 11.0 | 758 |

As is clear from these results, when the amount of the high-boiling non-volatile solvent was reduced, the spectral absorption characteristics and the heat fastness of the magenta dye-images obtained using Coupler (1) of this invention were scarcely changed which is different from the results obtained using known coupler (H) having an acylamino group at the 3-position of the pyrazolone ring. Furthermore, in using Coupler (1), when the amount of the high-boiling non-volatile solvent was reduced, the coupler was not crystallized in the photographic emulsion and stable color images having high transparency were obtained in contrast to the use of known coupler (C). From these results, it can be understood that by employing the magenta coupler of this invention, the amount of high-boiling non-volatile solvent used for dissolving the coupler can be reduced and thus the thickness of the photographic emulsion layers can be reduced.

EXAMPLE 4

A red-sensitive silver iodobromide (silver iodide 7 mol%) emulsion containing 1-hydroxy-2-tetradecyl-naphthamide was coated on a cellulose triacetate transparent film as a first layer in a thickness of 5.0 microns to provide $3.43 \times 10^{-2}$ mol/m$^2$ of silver halide and $2.86 \times 10^{-3}$ mol/m$^2$ of 1-hydroxy-2-tetradecylnaphthamide and then a gelatin solution containing 10 g of gelatin and 10 g of 2,5-di-tert-octylhydroquinone was further coated on the first layer as a second layer in a thickness of 1.0 micron so as to provide 0.04 g/m$^2$ of the 2,5-di-tert-octylhydroquinone.

A solution prepared by heating to 60°C a mixture of 15 g of Coupler (3) of this invention, 1.9 g of Coupler (11) of this invention, 8 ml of tricresyl phosphate, and 45 ml of ethyl acetate was added to 150 ml of an aqueous solution containing 15 g of gelatin and 0.4 g of sodium dodecylbenzenesulfonate at 60°C and the mixture was stirred as described in Example 1 to provide a coupler dispersion. The coupler dispersion thus prepared was mixed with 1 kg of a green-sensitive photographic emulsion containing $6 \times 10^{-1}$ mol of silver iodobromide (silver iodide 6 mol%) and 60 g of gelatin and after adding thereto 5 ml of a 3% acetone solution containing 2-hydroxy-4,6-dichloro-s-triazine sodium salt as a hardening agent and finally adjusting the pH thereof to 7.0, the resultant mixture was coated on the second layer as a third layer in a dry thickness of 5.4 microns. Thereafter, an aqueous gelatin solution containing yellow colloidal silver and 2,5-di-tert-octylhydroquinone was coated thereon as a fifth layer in a thickness of 1.5 microns and a blue-sensitive silver iodobromide emulsion (silver iodide 7 mol%) containing α-(p-methoxybenzoyl)-α-(N-phthalimido)-2-chloro-5-γ-(2,4-di-tert-amylphenoxy)butylamido acetanilide as a yellow dye forming coupler was coated thereon as a sixth layer in a thickness of 5.0 microns to provide $1.67 \times 10^{-2}$ mol/m$^2$ of silver halide and $1.60 \times 10^{-3}$ mol/m$^2$ of the yellow dye forming coupler, and finally a gelatin layer was coated as a protective layer in a thickness of 1.0 microns to provide a color photographic negative film.

When the color photographic film was exposed and subjected to the following development procedure, a color negative image having good gradation and image quality was obtained. Also, the blue density of the color image was substantially constant regardless of the extent of the exposure to green light, which showed that proper color correction was made.

| Processing Step | Temperature | Time |
|---|---|---|
| 1. Color Development | 38°C | 3 minutes |
| 2. Stop | " | 1 minute |
| 3. Washing | " | 1 minute |
| 4. Bleach | " | 2 minutes |
| 5. Washing | " | 1 minute |
| 6. Fix | " | 2 minutes |
| 7. Washing | " | 1 minute |
| 8. Stabilization | " | 1 minute |

The compositions of the processing solutions used in the above steps were as follows:

| Color Developer: | | |
|---|---|---|
| Sodium Hydroxide | 2 | g |
| Potassium Bromide | 0.4 | g |
| Sodium Sulfite | 2 | g |
| Sodium Chloride | 1 | g |
| Borax | 4 | g |
| Hydroxylamine Sulfate | 2 | g |
| Ethylenediamine Tetraacetic Acid | 2 | g |
| 4-{N-Ethyl-N(β-hydroxyethyl)amino}-2-methylaniline Sesquisulfate (monohydrate) | 4 | g |
| Water added to make | 1 | liter |
| Stop Solution: | | |
| Sodium Thiosulfate | 10 | g |
| Ammonium Thiosulfate (70%) | 30 | ml |
| Sodium Acetate | 5 | g |
| Acetic Acid | 30 | ml |
| Potassium Alum | 15 | g |
| Water added to make | 1 | liter |
| Bleach Solution: | | |
| Sodium Ferric Ethylenediamine Tetra-acetic Acid(dihydrate) | 100 | g |
| Potassium Bromide | 50 | g |
| Ammonium Nitrate | 50 | g |
| Boric Acid | 5 | g |
| Aqueous Ammonia to adjust the pH to | 5.0 | |
| Water added to make | 1 | liter |
| Fix Solution: | | |
| Sodium Thiosulfate | 150 | g |
| Sodium Sulfite | 15 | g |
| Borax | 12 | g |
| Glacial Acetic Acid | 15 | ml |
| Potassium Alum | 20 | g |
| Water added to make | 1 | liter |
| Stabilization Bath; | | |
| Boric Acid | 5 | g |
| Sodium Citrate | 5 | g |
| Sodium Metaborate (tetrahydrate) | 3 | g |
| Potassium Alum | 15 | g |
| Water added to make | 1 | liter |

EXAMPLE 5

A solution prepared by heating to 60°C a mixture of 5 g of each of Couplers (3), (4), (6), (9), (10), (11), (12), (13), (14), and (15), of this invention, 6 ml of tricresyl phosphate, and 8 ml of ethyl acetate was dispersed as described in Example 1 and after mixing with the photographic emulsion as described in Example 1, the resultant emulsion was coated and dried to give a color photographic film.

Each of the photographic films thus prepared was exposed and developed as described in Example 1, and a sharp color image having the absorption maximum as shown in Table 5 was obtained.

Table 5

| Coupler | Absorption Maximum (mµ) | Coupler | Absorption Maximum (mµ) |
|---|---|---|---|
| (3) | 533 | (4) | 535 |
| (6) | 527 | (9) | 528 |
| (10) | 540 | (11) | 540 |
| (12) | 540 | (13) | 535 |
| (14) | 533 | (15) | 527 |

While the invention has been described in detail and with reference to specific embodiments thereof, it will be apparent to one skilled in the art that various changes and modifications can be made therein without departing from the spirit and scope thereof.

What is claimed is:

1. A color photographic material comprising a support having thereon at least one silver halide emulsion layer containing a 3-anilino-5-pyrazolone magenta dye-forming coupler, said coupler having, the general formula

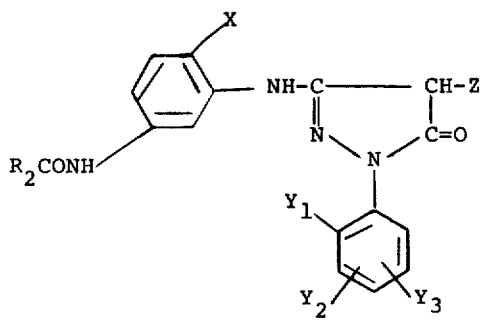

wherein $R_2$ represents a straight chain, branched chain, or cyclic alkyl group having 5 to 29 carbon atoms; X represents an alkoxyl group having 1 to 18 carbon atoms or a halogen atom; Z represents a hydrogen atom, a thiocyano group, an acyloxy group, an aryloxy group, an alkoxy group an arylazo group, a 2-aminoarylazoxy group, a 2-amidoarylazoxy group, a 2-aryltriazolyl group, an alkyl group, an alkylthio group, an arylthio group, a cycloalkylthio group, a carbon-containing heterocyclic monothio group having a 5 to 6 membered ring containing at least one hetero nitrogen, oxygen or sulfur atom in which the heterocyclic-moieties of the monothio group are incapable of forming a chromophoric compound; $Y_1$ represents a halogen atom, an alkyl group, or an alkoxy group; and $Y_2$ and $Y_3$, which may be the same or different, each represents a hydrogen atom, a halogen atom, an alkyl group, an alkoxy group, an aryloxy group, an alkoxycarbonyl group, an aralkoxycarbonyl group, a carboxyl group, a cyano group, a nitro group, or an acylamino group.

2. The color photographic material as set forth in claim 1 in which $R_2$ is a straight chain alkyl group.

3. The color photographic material as set forth in claim 2, in which said Z is a hydrogen atom or an arylazo group.

4. The color photographic material as set forth in claim 3, in which said X is a chlorine atom.

5. The color photographic material as set forth in claim 1, in which said magenta dye-forming coupler is
1-(2,4,6-trichlorophenyl)-3-(2-chloro-5-n-dodecanoylaminoanilino)-5-pyrazolone,
1-(2,4,6-trichlorophenyl)-3-(2-chloro-5-n-tetradecanoyl-aminoanilino)-5-pyrazolone, or
1-(2,4,6-trichlorophenyl)-3-(2-chloro-5-n-hexadecanoylaminoanilino)-5-pyrazolone.

6. The color photographic material as set forth in claim 1, in which said magenta dye-forming coupler is 1-(2,4,6-trichlorophenyl)-3-(2-chloro-5-n-alkylcarbonylaminoanilino)-4-α-naphthylazo-5-pyrazolone, said alkyl moiety having 7 to 17 carbon atoms.

7. The color photographic material as set forth in claim 1 wherein said carbon-containing heterocyclic monothio group contains 1-4 hetero nitrogen atoms.

8. A color photographic material comprising a support having thereon a green-sensitive silver halide emulsion layer containing a 3-anilino-5-pyrazolone magenta dye-forming coupler. a red-sensitive silver halide emulsion layer containing a cyan dye-forming coupler with a phenol or 1-naphthol nucleus, and a blue-sensitive silver halide emulsion layer containing a cyan dye-forming coupler with an acylacetamido group, said magenta dye-forming coupler having the general formula:

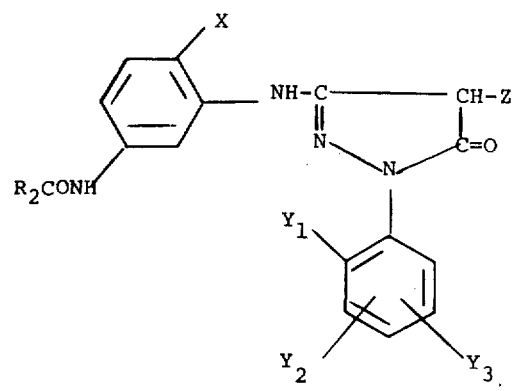

wherein $R_2$ represents a straight chain, branched chain, or cyclic alkyl group having 5 to 29 carbon atoms; X represents an alkoxyl group having 1 to 18 carbon atoms or a halogen atom; Z represents a hydrogen atom, a thiocyano group, an acyloxy group, an aryloxy group, an alkoxy group, an arylazo group, a 2-aminoarylazoxy group, a 2-amidoarylazoxy group, a 2-arylthriazolyl group, an alkyl group, an alkylthio group, an arylthio group, a cycloalkylthio group, a carbon-containing heterocyclic monothio group having a 5 to 6 membered ring containing at least one hetero nitrogen, oxygen or sulfur atom in which the heterocyclicmoieties of the monothio group are incapable of forming a chromophoric compound; $Y_1$ represents a halogen atom, an alkyl group, or an alkoxy group; and $Y_2$ and $Y_3$, which may be the same or different, each represents a hydrogen atom, a halogen atom, an alkyl group, an alkoxyl group, an aryloxy group, an alkoxycarbonyl group, an aralkoxycarbonyl group, a carboxyl group, a cyano group, a nitro group, or an acylamino group.

9. The color photographic material as set forth in claim 8 wherein said carbon-containing heterocyclic monothio group contains 1-4 hetero nitrogen atoms.

* * * * *